(12) United States Patent
Drmanovic

(10) Patent No.: US 11,541,219 B2
(45) Date of Patent: Jan. 3, 2023

(54) CAPPING DEVICE FOR DISINFECTING MEDICAL INJECTION MEMBRANES

(71) Applicant: DRMA GROUP INTERNATIONAL LLC, Palm City, FL (US)

(72) Inventor: Zoran Drmanovic, Palm City, FL (US)

(73) Assignee: DRMA Group International LLC, Palm City, FL (US)

( * ) Notice: Subject to any disclaimer, the term of this patent is extended or adjusted under 35 U.S.C. 154(b) by 133 days.

(21) Appl. No.: 15/644,963

(22) Filed: Jul. 10, 2017

(65) Prior Publication Data
US 2019/0009074 A1 Jan. 10, 2019

(51) Int. Cl.
| | |
|---|---|
| *A61M 39/16* | (2006.01) |
| *A61J 1/20* | (2006.01) |
| *A61L 2/16* | (2006.01) |
| *A61J 1/14* | (2006.01) |
| *A61L 2/26* | (2006.01) |
| *A61L 2/18* | (2006.01) |
| *A61J 1/10* | (2006.01) |

(52) U.S. Cl.
CPC .......... *A61M 39/162* (2013.01); *A61J 1/1475* (2013.01); *A61J 1/2048* (2015.05); *A61L 2/16* (2013.01); *A61L 2/18* (2013.01); *A61L 2/26* (2013.01); *A61J 1/10* (2013.01); *A61J 1/1406* (2013.01); *A61L 2202/123* (2013.01); *A61L 2202/24* (2013.01)

(58) Field of Classification Search
CPC .......... A61M 39/162; A61L 2/18; A61L 2/26; A61L 2/16; A61L 2202/123; A61L 2202/24; A61J 1/1475; A61J 1/2048; A61J 1/1406; A61J 1/10

See application file for complete search history.

(56) References Cited

U.S. PATENT DOCUMENTS

| | | | |
|---|---|---|---|
| 2,400,722 | A | 5/1946 | Swan |
| 4,340,052 | A | 7/1982 | Dennehey et al. |
| 4,417,890 | A * | 11/1983 | Dennehey ............. A61M 39/20 138/89 |
| 4,440,207 | A | 4/1984 | Genatempo et al. |
| 5,053,003 | A | 10/1991 | Dadson et al. |
| 5,242,425 | A | 9/1993 | White et al. |
| 5,295,975 | A | 3/1994 | Lockwood, Jr. |
| 5,324,264 | A | 6/1994 | Whitaker |

(Continued)

FOREIGN PATENT DOCUMENTS

| | | |
|---|---|---|
| EP | 0409180 A1 | 1/1991 |
| EP | 0520930 A1 | 12/1992 |

(Continued)

*Primary Examiner* — Regina M Yoo
(74) *Attorney, Agent, or Firm* — Dmitry Zuev, Esq.

(57) ABSTRACT

A device for disinfection of a medical injection port is provided. The device includes a capping portion having an inner surface, a hollow portion having an inner surface, a proximal opening, and a distal opening, a connector coupling the capping portion of the device to the hollow portion thereof, and a disinfecting absorbent material disposed inside the capping portion of the device. The connector permits movement of the capping portion between a fully-seated position on the hollow portion of the device, and a position apart from the proximal opening thereof to permit ingress to the medical injection port.

10 Claims, 7 Drawing Sheets

(56) References Cited

U.S. PATENT DOCUMENTS

| | | | |
|---|---|---|---|
| 5,429,612 A | 7/1995 | Berthier | |
| 5,681,283 A | 10/1997 | Brownfield | |
| 5,792,120 A | 8/1998 | Menyhay | |
| 5,885,249 A | 3/1999 | Irisawa | |
| 5,947,890 A * | 9/1999 | Spencer | A61M 25/104 600/3 |
| 6,045,539 A | 4/2000 | Menyhay | |
| 6,171,287 B1 | 1/2001 | Lynn et al. | |
| 6,322,540 B1 | 11/2001 | Grabis et al. | |
| 6,391,003 B1 | 5/2002 | Lesch, Jr. | |
| 6,409,706 B1 | 6/2002 | Loy | |
| 6,547,764 B2 | 4/2003 | Larsen et al. | |
| 6,582,408 B1 | 6/2003 | Buch-Rasmussen et al. | |
| 6,908,460 B2 | 6/2005 | Distefano | |
| 7,682,561 B2 | 3/2010 | Davis et al. | |
| 7,815,611 B2 | 10/2010 | Giambattista et al. | |
| 7,931,877 B2 | 4/2011 | Steffens et al. | |
| 8,065,773 B2 | 11/2011 | Vaillancourt et al. | |
| 8,069,523 B2 | 12/2011 | Vaillancourt et al. | |
| 8,172,825 B2 | 5/2012 | Solomon et al. | |
| 8,177,761 B2 | 5/2012 | Howlett et al. | |
| 8,197,749 B2 | 6/2012 | Howlett et al. | |
| 8,231,587 B2 | 7/2012 | Solomon et al. | |
| 8,298,196 B1 | 10/2012 | Mansour | |
| 8,328,767 B2 | 12/2012 | Solomon et al. | |
| 8,336,151 B2 | 12/2012 | Kerr et al. | |
| 8,336,152 B2 | 12/2012 | Vaillancourt et al. | |
| 8,343,112 B2 | 1/2013 | Solomon et al. | |
| 8,491,546 B2 | 7/2013 | Hoang et al. | |
| 8,523,830 B2 | 9/2013 | Solomon et al. | |
| 8,523,831 B2 | 9/2013 | Solomon et al. | |
| 8,641,681 B2 | 2/2014 | Solomon et al. | |
| 8,647,308 B2 | 2/2014 | Solomon et al. | |
| 8,647,326 B2 | 2/2014 | Solomon et al. | |
| 8,671,496 B2 | 3/2014 | Vaillancourt et al. | |
| 8,696,820 B2 | 4/2014 | Vaillancourt et al. | |
| 8,734,384 B2 | 5/2014 | Boyd et al. | |
| 8,740,864 B2 | 6/2014 | Hoang et al. | |
| 8,784,388 B2 | 7/2014 | Charles et al. | |
| 8,961,475 B2 | 2/2015 | Solomon et al. | |
| 8,999,073 B2 | 4/2015 | Rogers et al. | |
| 9,039,989 B2 | 5/2015 | Liu et al. | |
| 9,079,692 B2 | 7/2015 | Solomon et al. | |
| 9,114,915 B2 | 8/2015 | Solomon et al. | |
| 9,186,707 B2 | 11/2015 | Vaillancourt et al. | |
| 9,192,449 B2 | 11/2015 | Kerr et al. | |
| 9,259,284 B2 | 2/2016 | Rogers et al. | |
| 9,283,367 B2 | 3/2016 | Hoang et al. | |
| 9,283,368 B2 | 3/2016 | Hoang et al. | |
| 9,283,369 B2 | 3/2016 | Ma et al. | |
| 10,195,110 B2 * | 2/2019 | Drmanovic | A61J 1/065 |
| 10,376,686 B2 * | 8/2019 | Burkholz | A61M 39/16 |
| 2007/0093762 A1 * | 4/2007 | Utterberg | A61M 39/02 604/256 |
| 2008/0177250 A1 | 7/2008 | Howlett et al. | |
| 2009/0137969 A1 | 5/2009 | Colantonio et al. | |
| 2009/0307449 A1 | 12/2009 | Prahlad et al. | |
| 2010/0272379 A1 | 10/2010 | Hu et al. | |
| 2011/0054440 A1 | 3/2011 | Lewis | |
| 2012/0302970 A1 | 11/2012 | Tennican | |
| 2013/0171030 A1 | 7/2013 | Ferlic et al. | |
| 2015/0360021 A1 | 12/2015 | Limdico et al. | |
| 2017/0232121 A1 | 8/2017 | Chiu et al. | |
| 2018/0055962 A1 * | 3/2018 | Drmanovic | A61L 2/235 |
| 2018/0064604 A1 | 3/2018 | Drmanovic | |
| 2018/0071508 A1 * | 3/2018 | Drmanovic | A61M 39/16 |
| 2018/0085568 A1 * | 3/2018 | Drmanovic | A61M 5/3134 |

FOREIGN PATENT DOCUMENTS

| | | |
|---|---|---|
| EP | 0832661 A2 | 4/1998 |
| EP | 1336419 A1 | 8/2003 |
| WO | 2015120336 A1 | 8/2015 |

* cited by examiner

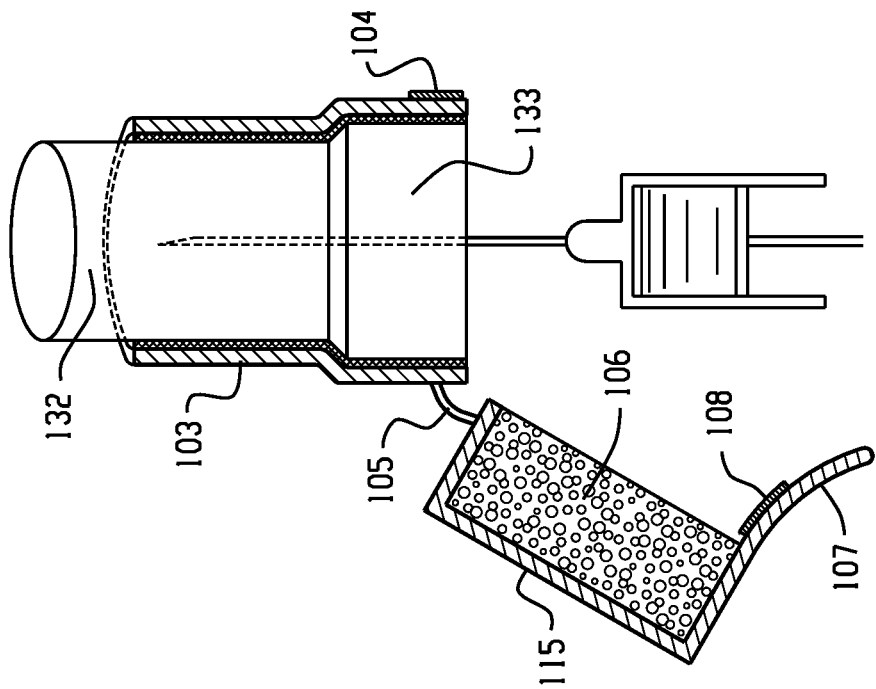
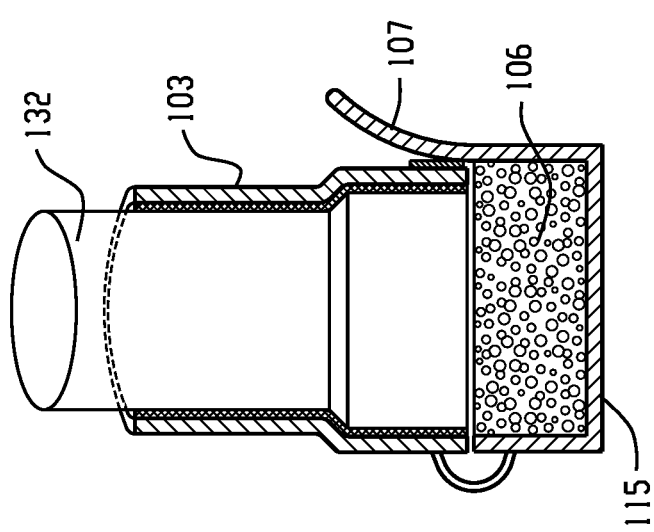
Fig. 4A
Fig. 4B

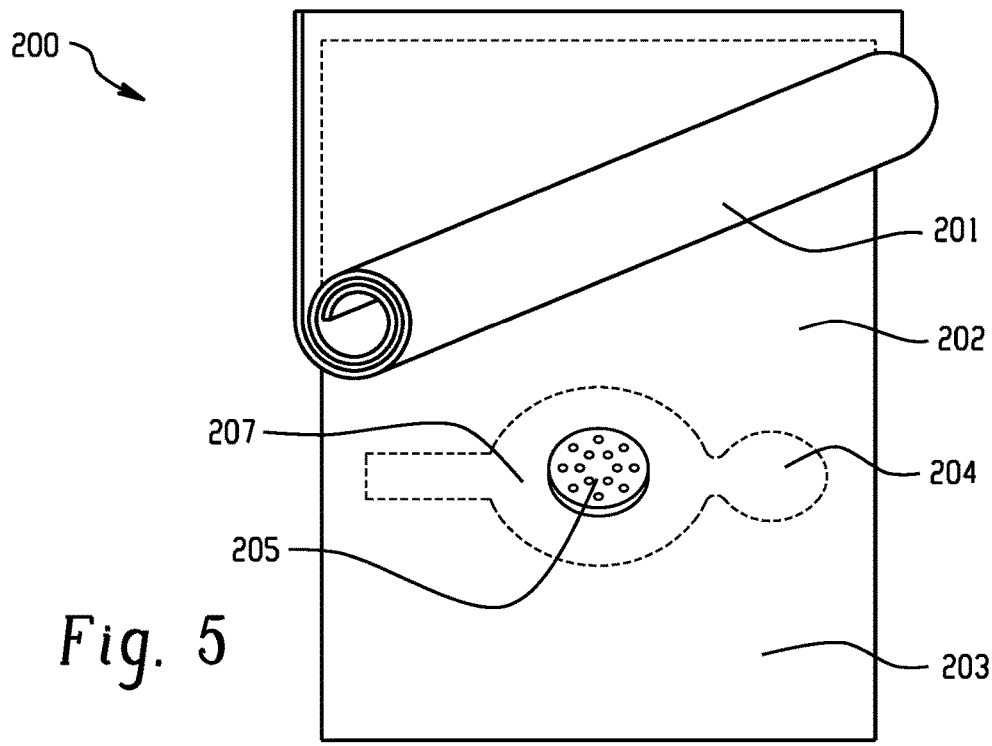
Fig. 5
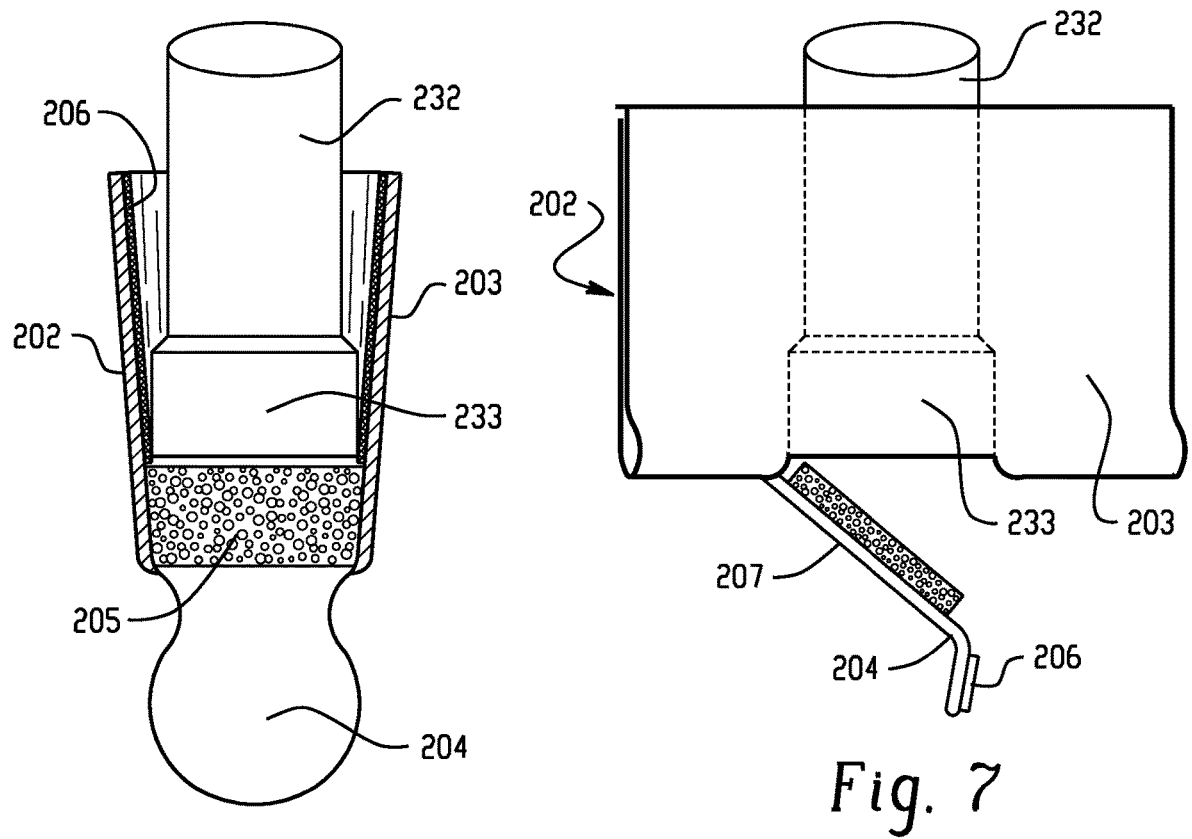
Fig. 6
Fig. 7

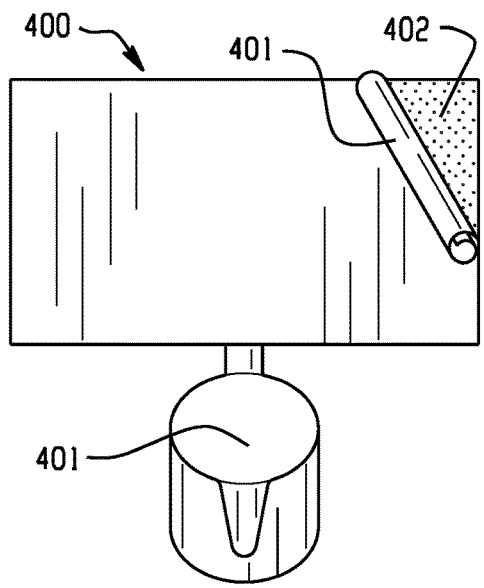
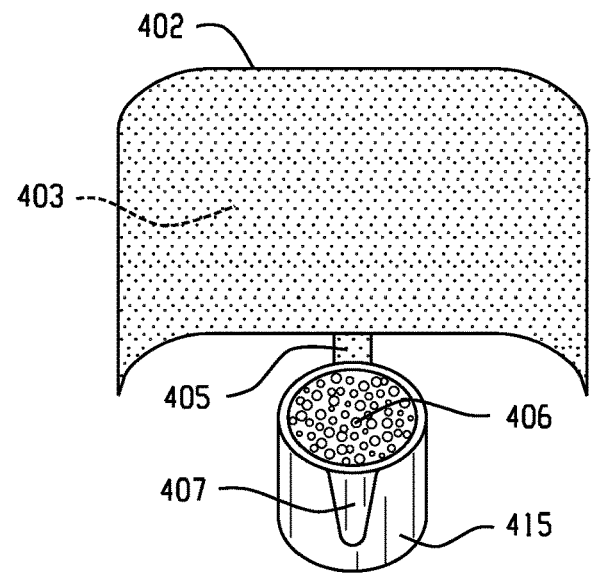
Fig. 12A    Fig. 12B
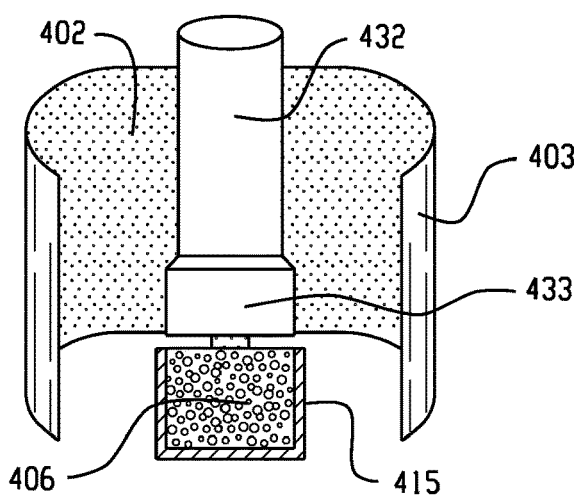
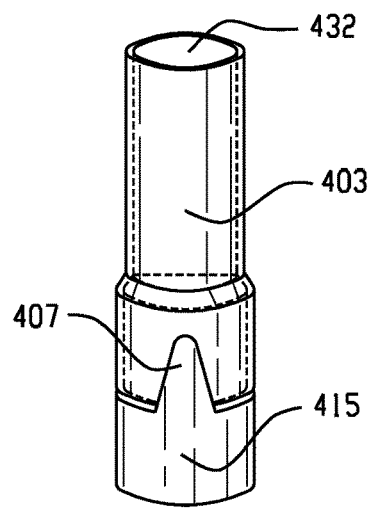
Fig. 12C    Fig. 12D
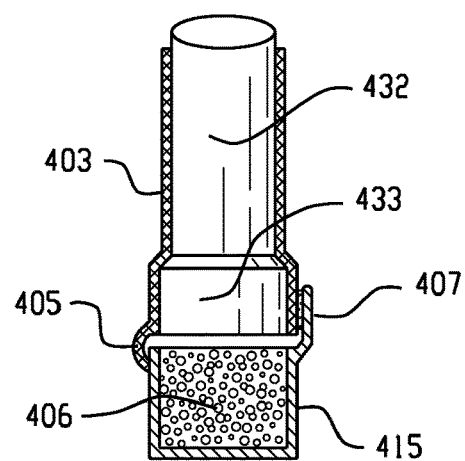
Fig. 12E

CAPPING DEVICE FOR DISINFECTING MEDICAL INJECTION MEMBRANES

BACKGROUND

The present invention generally relates to a self-disinfecting capping device, and more specifically, to a capping device for disinfecting a medical injection membrane.

Most solutions for intravenous use are kept inside plastic intravenous (IV) bags. A majority of these bags have two ports. The first port is used for intravenous tubing insertion and allows the solution inside the bag to run through intravenous tubing into the patient's bloodstream. The second port is an injection port, which contains a rubber membrane, which can be penetrated by a sterile needle. Subsequently, a medication can be injected into the bag, or a solution can be drawn from the bag. In order to keep the rubber membrane disinfected and prevent contamination of the bag, medical professionals ordinarily wipe the rubber membrane with a pad containing a disinfecting agent. When faced with time constraints or stressful situations, only the most diligent specialists do so every time the medication is drawn or injected. Sometimes during a surgery, a medical provider has to repeatedly draw the medication from the same bag within a period of a few hours. For example, providers need to repeatedly access the injection port of a bag containing Neosynephrine in order to draw the medication into the syringe. Between these drawings, rubber injection membrane may be exposed to bacteria from the environment or may be accidently contaminated by blood or body fluids. This creates a risk of contamination of the content of the bag by introduction of bloodstream infections if aseptic techniques are not strictly followed. Most IV bags have a tubing port and injection port next to each other at the bottom of the bag. Some IV bags only have a tubing port at the bottom of the bag, while the injection membrane (often called "belly button" membrane) is located above the tubing port. Injection membranes are also found on IV tubings and other medical supplies. The same principle of covering with self-disinfecting caps applies to all membranes with some variations in size and shape.

It is a custom for a medical professional to always use a new, sterile syringe and a new, sterile needle to access the injection membrane on IV bags. However, even when the providers do so, it is still possible to introduce an infection if the rubber septum is contaminated. Occasionally, under pressure and stress, providers may utilize the same needle and the same syringe, which may be contaminated with blood or bacteria. This practice causes bag contamination and may introduce bacteria into the bloodstream of a patient.

While it is not recommended to use the same needle and syringe to penetrate injection membrane because of the risks described above, there are circumstances where the medication is frequently drawn more than once by the same syringe and needle. Examples include drawing Neosynephrine, Norepinephrine, or Epinephrine from a 250 milliliter IV bag into the syringe.

Thus, there remains a need for a convenient and reliable disinfecting device that would allow medical professionals to carry out multiple drawings from or injections into the same IV bag, tubing, or any other product containing an injection membrane with 100% antiseptic techniques compliance.

SUMMARY

In an embodiment, a device for disinfection of a medical injection port is provided. The device includes a capping portion having an inner surface, a hollow portion having an inner surface, a proximal opening, and a distal opening, a connector coupling the capping portion of the device to the hollow portion thereof, and a disinfecting absorbent material disposed inside the capping portion of the device. The connector permits movement of the capping portion between a fully-seated position on the hollow portion of the device, and a position apart from the proximal opening thereof to permit ingress to the medical injection port.

The device may be configured for attachment to the medical injection port to bring the disinfecting absorbent material of the capping portion in contact with the medical injection port.

The capping portion may include a covering member and a sidewall disposed substantially perpendicular to and in contact with the covering member.

The hollow portion may include a supporting member having the proximal opening and a sidewall disposed substantially perpendicular to and in contact with the supporting member.

The proximal opening may be located approximately at the center of the supporting member. The proximal opening is substantially circular.

The proximal opening may be disposed concentrically to the internal surface of the hollow portion.

The disinfecting absorbent material may be affixed to the inner surface of the capping portion of the device. The disinfecting absorbent material may be soaked with a disinfecting agent.

The connector may include a hinge providing a pivotal connection between the capping portion of the device and the hollow portion thereof. The capping portion in the fully-seated position may be disposed in contact with the supporting member of the hollow portion to provide a seal. The disinfecting absorbent material of the capping portion in the fully-seated position may extend through the proximal opening of the supporting member of the hollow portion.

The hollow portion may further include a sealing member disposed on and in contact with the supporting member of the hollow portion.

The disinfecting absorbent material in the fully-seated position may completely cover the proximal opening of the hollow portion.

The capping portion may include a fastening member for attachment of the capping portion of the device to the hollow portion thereof in the fully-seated position.

The connector may be adapted such that, when the capping portion is disposed at the position apart from the proximal opening of the hollow portion of the device in the absence of an external force, the connector brings the capping portion to the fully-seated position. The connector comprises a flexible material.

In another embodiment, a method for disinfecting a medical injection port is provided. According to the method, a device for disinfection of a medical injection port is provided. The device includes a capping portion having an inner surface, a hollow portion having an inner surface, a proximal opening, and a distal opening, a connector coupling the capping portion of the device to the hollow portion thereof, and a disinfecting absorbent material disposed inside the capping portion of the device. The connector permits movement of the capping portion between a fully-seated position on the hollow portion of the device, and a position apart from the proximal opening thereof to permit ingress to the medical injection port. The method further includes attaching the device to the medical injection port to bring the disinfecting absorbent material in contact with the medical injection port.

The method may further include applying an external force to the device to move the top portion thereof from the fully-seated position to the position apart from the proximal opening of the hollow portion, inserting a medical implement through the proximal opening of the hollow portion of the device into the medical injection port, and withdrawing at least a portion of a content of the medical injection port into the medical implement.

The method may yet further include moving the capping portion of the device from the position apart from the proximal opening to the fully-seated position to bring the disinfecting absorbent material in contact with the medical injection port.

BRIEF DESCRIPTION OF THE DRAWINGS

The above and other aspects and features of the present disclosure will become more apparent by describing in detail exemplary embodiments thereof with reference to the attached drawings, in which:

FIG. 4A is a view of the capping device, according to an embodiment, secured around the injection membrane with the cap closed;

FIG. 4B shows the same capping device, according to an embodiment, around the injection membrane with the cap opened;

FIG. 5 is a view of another variation of the capping device, according to an embodiment, with the protective (peelable) foil partially removed;

FIG. 6 is a cross-sectional view of the capping device, according to an embodiment, after the front side and the back side of the device were folded around injection membrane;

FIG. 7 is a front view of the device, according to an embodiment, secured around the injection membrane with the cap opened and the membrane exposed for injection or withdrawal of medication;

FIG. 12A is a view of another variation of the capping device, according to an embodiment, wherein the protective (peelable) foil is partially removed;

FIG. 12B is a view of another variation of the capping device, according to an embodiment, wherein the protective (peelable) foil is completely removed, and wherein the capping device is ready to be placed around the injection port;

FIG. 12C is a view of another variation of the capping device, according to an embodiment, wherein the capping device is partially wrapped around the injection port;

FIG. 12D is a view of another variation of the capping device, according to an embodiment, wherein the capping device is completely wrapped around the injection port, and wherein the side extension of the cap is affixed to the injection port; and FIG. 12E is a cross-sectional view of another variation of the capping device, according to an embodiment, wherein the capping device is applied to the injection port.

DETAILED DESCRIPTION

Figure 2:
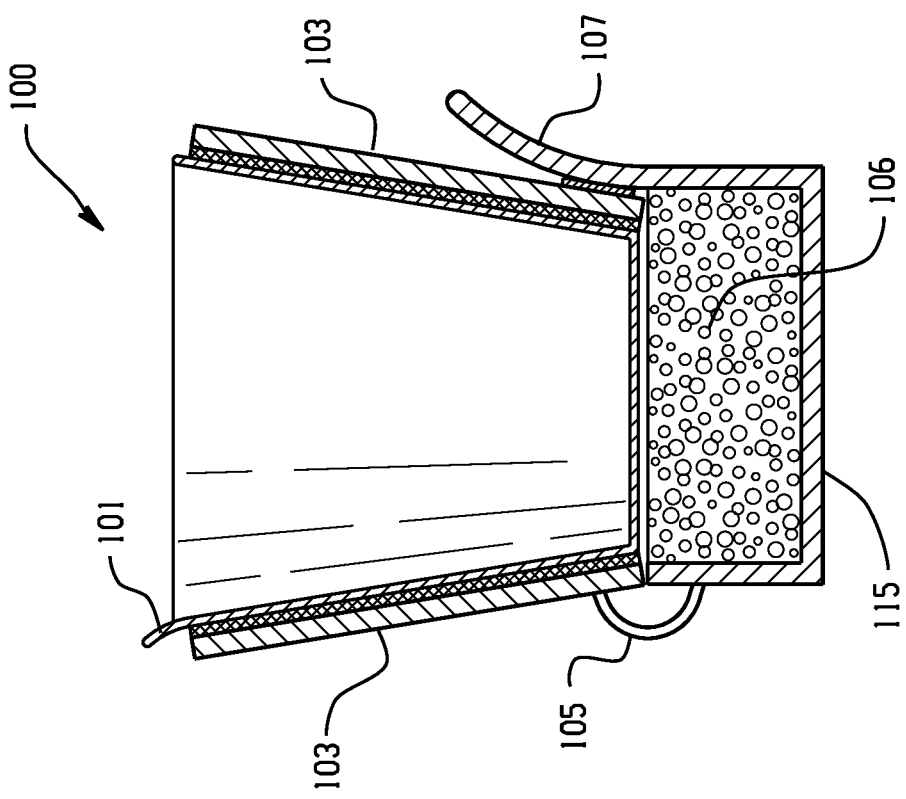
FIG. 2 is a view of the capping device, according to an embodiment, before its first use.

Reference will now be made in detail to the embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The terms "substantially" and "approximately" as used herein are inclusive of the stated value and mean within an acceptable range of deviation for the particular value as determined by one of ordinary skill in the art, considering the measurement in question and the error associated with measurement of the particular quantity (i.e., the limitations of the measurement system). For example, "substantially" and "approximately" can mean within one or more standard deviations, or within ±30%, 20%, 10%, 5% of the stated value.

In an embodiment, a device for disinfection of a medical injection port is provided. The device includes a capping portion having an inner surface, a hollow portion having an inner surface, a proximal opening, and a distal opening, a connector coupling the capping portion of the device to the hollow portion thereof, and a disinfecting absorbent material disposed inside the capping portion of the device. The connector permits movement of the capping portion between a fully-seated position on the hollow portion of the device, and a position apart from the proximal opening thereof to permit ingress to the medical injection port.

The device may be configured for attachment to the medical injection port to bring the disinfecting absorbent material of the capping portion in contact with the medical injection port.

Figure 1:
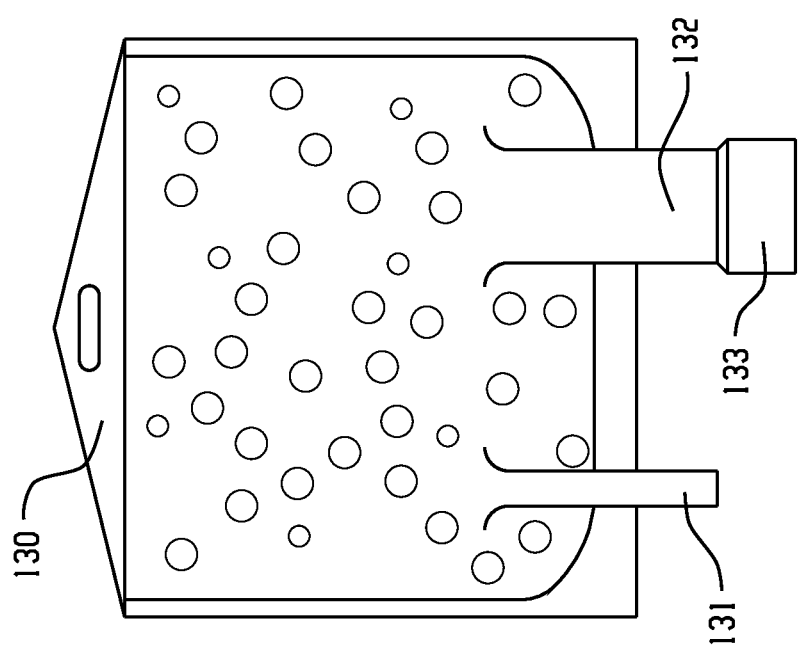
FIG. 1 is a view of a common intravenous solution bag before its first use.

FIG. 1 shows a typical IV bag 130 with an IV tubing port 131 and an injection port 132. Located at the bottom of the injection port 132 is the injection membrane 133. The injection membrane IV is usually made of rubber or any other suitable material. The size of the IV bag 130 may vary from 50 milliliters (ml) to several liters.

FIG. 2 shows a capping device 100, according to an embodiment, before its first use. The capping device 100 includes a cap portion (cap) 115 and a hollow portion 103, which may be placed and affixed around the injection membrane 133. Depending on the type of the injection port and membrane, the funnel may have a different shape in order to properly fit the shape and size of the injection port and the membrane. The hollow portion may be cylindrical or may have a shape of a funnel. For simplicity, the hollow portion 103 will thereafter be referred to as a "funnel". In an embodiment, the cap 115 may have circular shape since most of the injection membranes are circular (round). A peelable foil 101 may cover the inner surface of the funnel 103 to protect the inner surface from contamination. The inner surface of the funnel 103 may be covered with an adhesive material 102 to better attach the funnel 103 to the injection port. The peelable foil protects the adhesive material 102 from drying, keeps the inner surface of the funnel sterile until its first use, and prevents the cap portion 103 of the device from moving away from the hollow portion 103. Without the foil, the funnel may collapse, and the adhesive material 102 from the opposing sides may come together and close the funnel. The foil 101 may be made of various suitable materials known in the art.

A connector 105 (hereinafter referred to as a "loop") may be disposed on the side of the device and may provide a pivotal connection between the funnel 103 and the cap 115. Both the funnel 103 and the cap 115 may be made of some light weight material such as foil, tape, or light plastic. The material may provide a fluid barrier to avoid leakage and loss of the disinfecting agent. Located inside the cap 115 is a disinfecting pad 106, which may be soaked with a disinfecting agent. The disinfecting pad 106 may be affixed to the inner surface of the cap 115. The disinfecting pad 106 corresponds to the size and shape of the inferior surface of most of the commercially available injection membranes. Opposite to the loop 105 is a side extension 107, which may be an adhesive foil. The side extension 107 may have a different shape and size and may contain an adhesive material 108 located at the bottom surface thereof. The side extension 107 is located on the side opposite of the loop 105. When the device is in a fully-seated (rested or closed) position, the side extension 107 may be used to close the device by affixing to the funnel 103. The area on the funnel 104, which receives the side extension, is made of some material which allows multiple opening and closing. It is desirable that the adhesive material on the bottom surface of the side extension 107 also allows multiple taping and untaping (gluing and ungluing, removing and reaffixing). The capping device 100 would come in a sterile, sealed package, and the sterilization technique has to be carefully chosen without affecting the quality of the disinfecting agent.

Figure 3B:
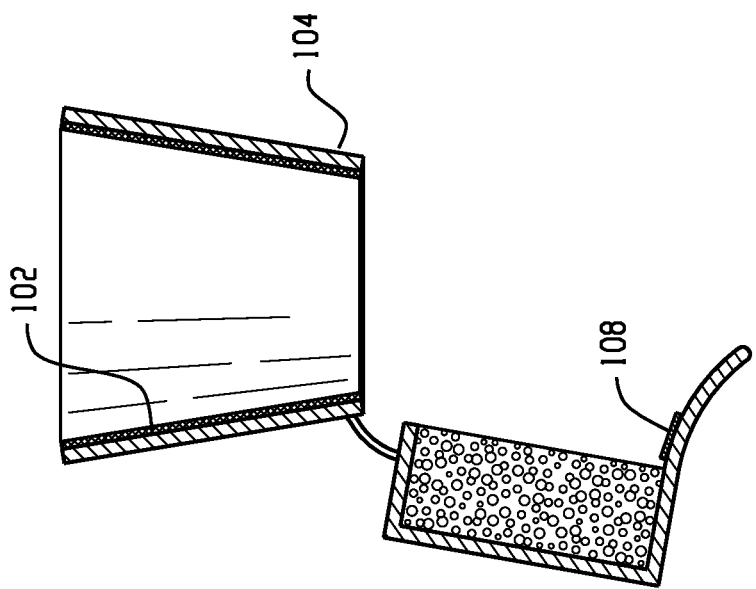
FIG. 3B is a view of the same capping device, according to an embodiment, with the cap opened.
Figure 3A:
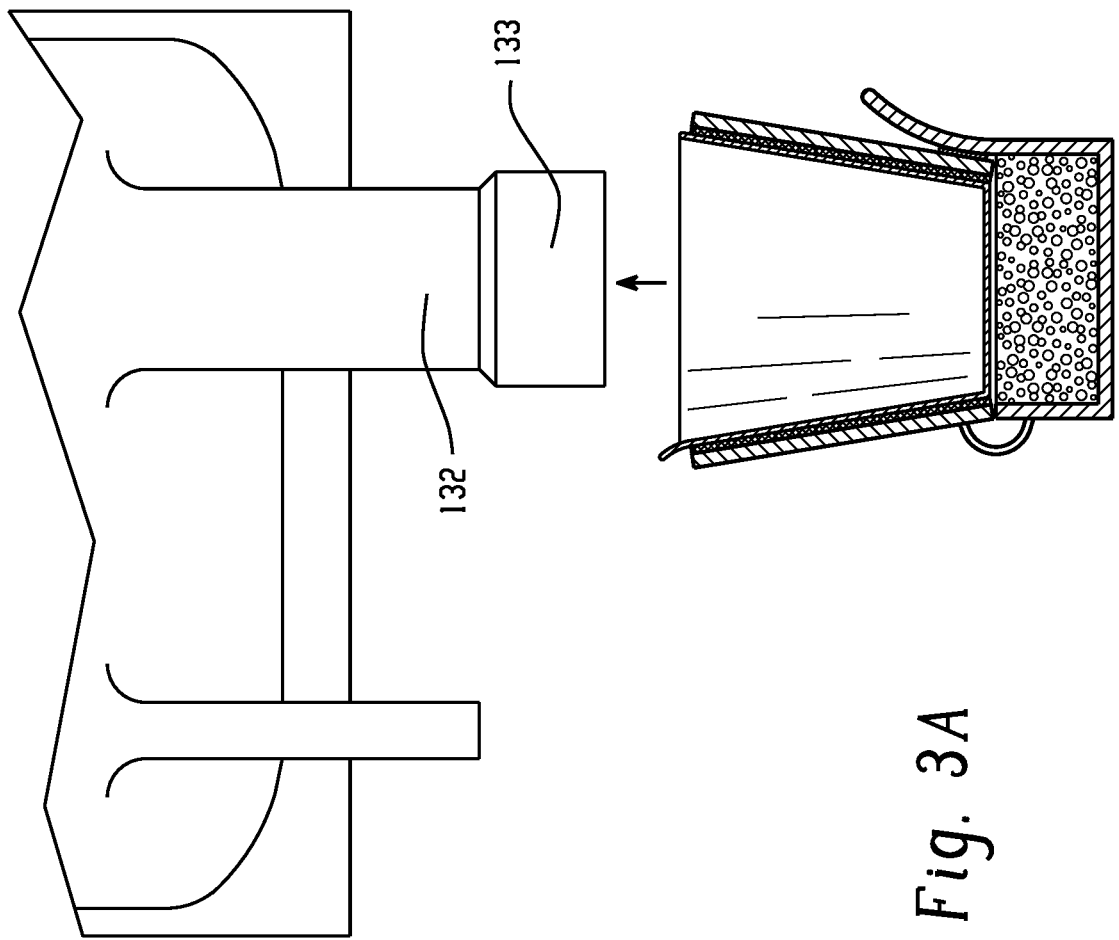
FIG. 3A is a view of the capping device, according to an embodiment, coming in close contact with the injection membrane after the peelable foil was removed.

FIG. 3A shows a typical IV bag and the capping device 100 after the peelable foil 101 has been removed. The device is now ready to be placed around the injection membrane 133 of the port. The adhesive material is shown covering the inside surface of the funnel and is used to form a good connection with the injection port 132 and the injection membrane 133. In FIG. 3A, the device is shown in a closed, fully-seated position. FIG. 3B shows the same device in the open form. In order to open the device, a provider peels off the side extension 107 and moves the cap 115 away. The loop 105 keeps the funnel 103 and the cap 115 together. The length of the loop 105 is short since it allows the opening of the cap 115, and more importantly, keeps the disinfecting pad 106 in contact with the injection membrane 133 when the capping device 100 is in a closed position.

FIG. 4A shows the capping device 100 closed and applied around the injection port 132 and the injection membrane 133. The funnel 103 needs to be wider than the injection membrane. The funnel may be made of a light material that easily compresses around injection ports and membranes of various shapes and sizes (differences in size of injection membranes may somewhat vary). A provider may just apply slight pressure around the funnel 103 until there is a good bond between the funnel 103, the injection port 133, and the injection port 132. The disinfecting pad 106 can be made from any suitable material having good absorbing ability, for example, a sponge. The disinfecting pad 106 corresponds in size and shape to the size and shape of the inferior surface of the known injection membranes. The inner surface of the cap 115 creates a hollow (chamber) in which the disinfecting pad 106 is located. The amount of the disinfecting agent is usually small and the good absorbing ability of the disinfecting pad 106 should be sufficient to absorb all of the disinfecting agent. The disinfecting pad 106 is soaked with the disinfecting agent such as povidone iodine, alcohol, or chlorhexidine, or any combination of the disinfecting agents that provides antiseptic, antibacterial, or antiviral properties. The disinfecting pad 106 can be made of a non-woven material such as polyester, silicone, cotton, polyurethane, or any other absorbent material known in the art. The amount of the absorbent material may vary. FIG. 4B shows the capping device 100 in an open position, in which the device is applied around the injection membrane 133 and the injection port 132. Since the device 100 is open, the inferior surface of the injection membrane 133 is available for a needle to penetrate it and for the medication to be drawn or injected. FIG. 4B shows a needle penetrating the injection membrane 133, which has been sterilized by the disinfecting pad 106, and which is now inside the injection port 132. The funnel 103 is disposed around the injection port and the membrane, and the cap 115 is pushed aside. FIG. 4B also allows a good view of the receptive area 104 of the funnel 103, which is made of material that allows multiple taping and untaping. The size and shape of the receptive area 104 corresponds to the size and shape of the side extension 107. The loop 105 keeps the funnel 103 and the cap 115 together. The loop (which may be a bend) is made of a durable material to prevent its breakage. By keeping the parts together, the loop 105 also reminds a medical provider to close the device after each use. As a result, forced compliance with aseptic techniques is achieved, and the rubber injection membrane 133 is always kept sterile. The loop (bend) 105 is located opposite to the side extension 107. All these elements may be built from a foil or tape which is durable and which provides a sufficient fluid barrier to prevent leakage and evaporation of the disinfecting agent. The side extension 107 may have a different shape and size and may contain an adhesive material located at its bottom surface. When the device is in a fully-seated (rested, closed) position, the side extension 107 may be used to close the device by affixing it to the receptive area 104 of the funnel 103.

FIG. 5 shows another version of the capping device 200, according to an embodiment, which serves the same purpose as the embodiment described above. The capping device 200 may include a front panel 203, a back panel 202, and a cap 207. The capping device is shown from the side that comes in contact with an injection port 232 and an injection membrane 233. Before the first use, this side is protected with a peelable foil 201, and in this view, the foil is shown partially peeled. This side of the capping device is covered with an adhesive material except for the disinfecting pad 205 which is soaked with the disinfecting agent. The cap 207 is shown in a dotted line since it is partially cut, and therefore, the cap 207 is partially separated from the front and back panel. This separation allows the cap 207 to cover and disinfect the injection membrane 233 when the injection membrane is not in use, and to move the cap 207 away from the injection membrane when it is necessary to withdraw or inject the medication. The size and shape of the disinfecting pad correspond to the size and shape of the most known injection membranes. The size and shape of the cap 207 is such that it allows it to encircle the disinfecting pad and to prevent the leakage and evaporation of the disinfecting agent present in the pad.

FIG. 6 shows a cross-sectional view of the capping device 200. The front panel 203 is covered inside with an adhesive material and is shown ready to be pushed and glued to the front side of the injection port 232 and the front side of the injection membrane 233. The back panel 202 is also shown with the adhesive material on its inside surface ready to be glued to the posterior side of the injection port 232 and the membrane 233. The disinfecting pad 205 soaked with the disinfecting agent is illustrated in contact with the injection membrane's inferior surface (where the injection of the medication occurs). This arrangement keeps the membrane sterilized when the device is not in use. It is very important that the disinfected pad 205 contacts the inferior surface of the injection membrane 233 before the front panel 203 and the back panel 204 panel are pushed and affixed to the injection port 232. Otherwise, there would be an empty space between the membrane 233 and the disinfecting pad 205. The side extension 204 is covered with an adhesive material, and the adhesive material has to allow multiple taping and untaping (gluing and ungluing, affixing and removing) in order to move the disinfecting pad 205 away when the injection membrane 233 is in use. The side of the cap 207 opposite to the side extension 204 may be permanently affixed to the front panel 203 and the back panel 202.

FIG. 7 is the front view of the disinfecting apparatus 200 affixed to the injection port 232 and the injection membrane 233 (a dotted line represents parts of the port and membrane that cannot be seen since they are covered with the front panel 203 and the back panel 202). The cap 207 is shown opened and the inferior surface of the injection membrane 233 is now available for injection or withdrawal of the medication. Since the side of the cap 207 opposite to the side extension 204 is permanently affixed to the panel, the cap 207 stays in close proximity to the injection membrane, thus reminding the provider to close the cap 207 after use to ensure compliance with sterile techniques. Indeed, the likelihood that a provider would not notice that the cap 207 is hanging and would not close it is extremely low. The side extension 204 is shown with the adhesive material disposed on its upper surface, which comes into contact with the front panel 203 and the back panel 202, and optionally, with the side of the injection membrane 233, but not with its inferior surface, which is covered and sterilized by the disinfecting pad 205.

Figure 8:
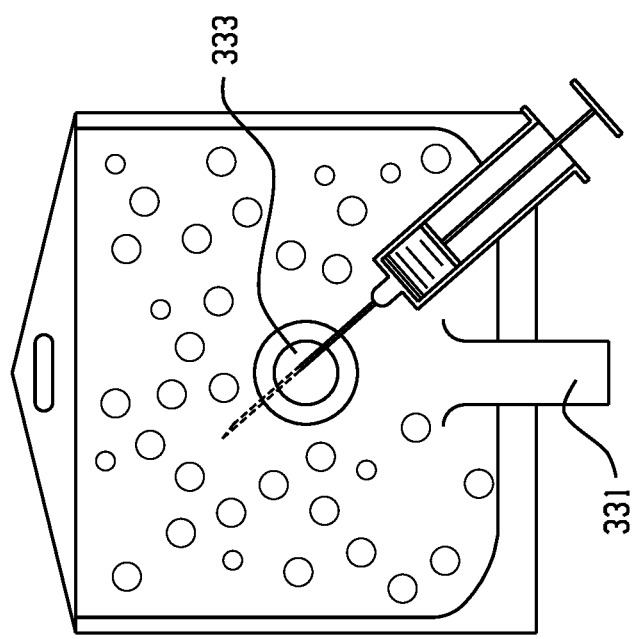
FIG. 8 is a view of another type of common intravenous solution bag where the injection membrane is not located at the bottom of the bag but is located on the front side.

FIG. 8 is a view of another type of a commonly used IV bag, which has an IV tubing port at the bottom thereof. This port is used to connect the IV bag with the IV tubing and to deliver an IV solution into the patient's bloodstream. This type of an IV bag has the injection membrane 333 located on its front size, which is commonly called a "belly button" membrane. It is usually round, slightly elevated above the level of the IV bag, and is often made of rubber. The "belly button" membrane is used for injection of the medications into the bag and withdrawal of the medication from the bag.

Figure 9:
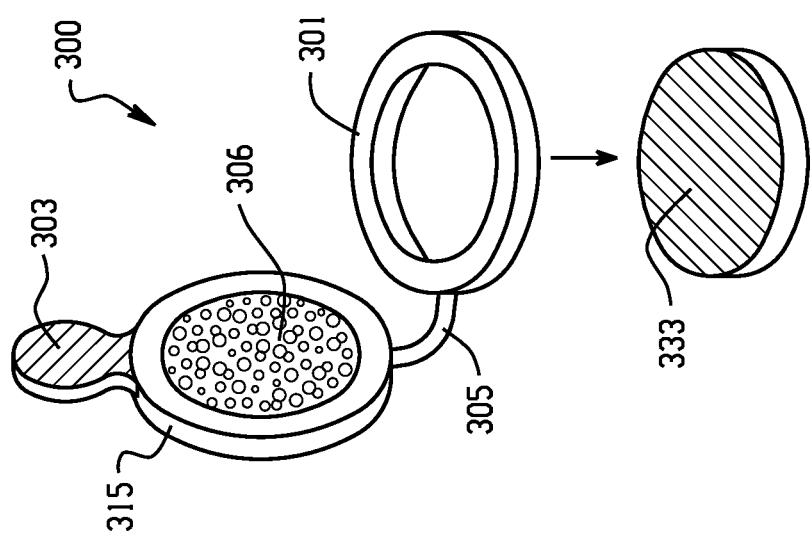
FIG. 9 is a view of the capping device, according to another embodiment, in a position apart from the injection membrane with the peelable foil removed, wherein the capping device, according to an embodiment, is ready to be placed at the top of the injection membrane.

FIG. 9 is a view of the capping device 300 with the cap 315 opened and the base 301 located above the injection membrane 333. At the bottom of the base 301 is an adhesive material, which helps to create a bond between the base 301 and the injection membrane 333. The cap has a side extension 303 covered with the adhesive material, which keeps the cap closed and the injection membrane sterilized when the device is not in use. Located inside the cap 315 is a disinfecting pad 306, which may be soaked with a disinfecting agent. The disinfecting pad 306 may be affixed to the inner surface of the cap 315. The disinfecting pad 306 corresponds in size and shape to those of most commercially available "belly button" injection membranes. A connector (which may be a loop or a band) 305 may be disposed on the side of the device and may provide a pivotal connection between the base 301 and the cap 315. Both the base 301 and the cap 315 are made of some light weight material such as foil, tape, or light plastic. The material may provide a fluid barrier to avoid leakage and loss of the disinfecting agent.

Figure 10A:
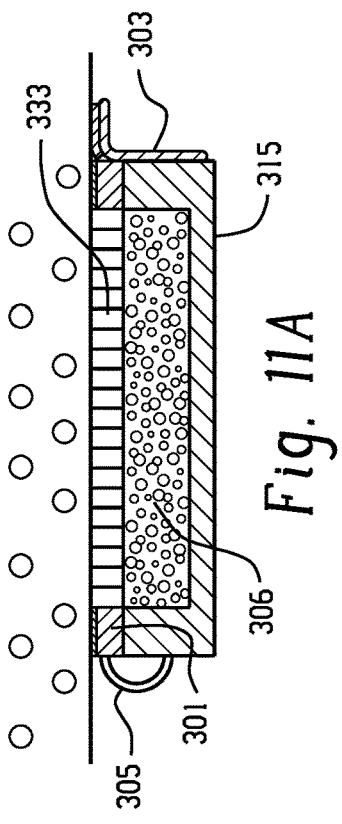
FIG. 10A shows a typical injection membrane disposed on an IV bag.
Figure 10B:
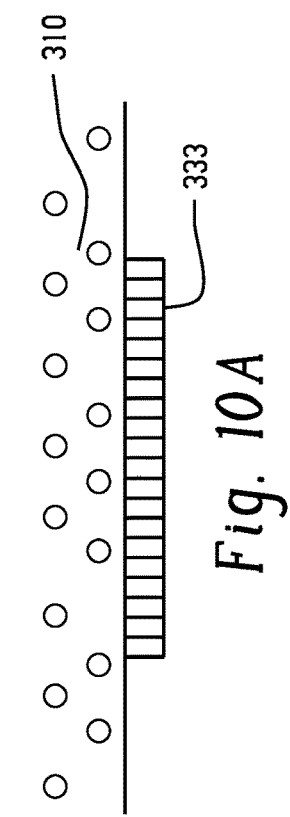
FIG. 10B is a cross-sectional view of the capping device, according to another embodiment, wherein the capping device, comes into close contact with the injection membrane after the peelable foil has been removed.
Figure 10C:
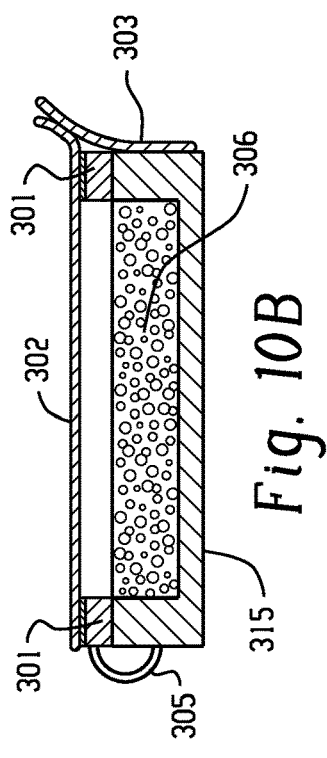
FIG. 10C is a cross-sectional view of the capping device, according to another embodiment, before its first use, before the peelable foil has been removed.

FIG. 10A shows a cross-sectional view of the injection membrane 333. Fluid 310 is shown inside the IV bag. FIG. 10B displays the capping device 300 before its first use with the peelable foil 302 covering the bottom of the device. The foil 302 is round and corresponds in diameter to the diameter of the base 301. The peelable foil 302 protects the adhesive material 308 and the disinfecting pad 306 from drying and keeps the interior of the device sterile. The tip of the side extension 303 may be covered with the same peelable foil 302 since it also contains the adhesive material. Alternatively, the tip of the side extension 303 may have its own peelable foil, which may be removed before the first use of the device. FIG. 10C shows the capping device 300 after the peelable foil 302 has been removed, when the device is ready to be applied around the injection membrane 333. The adhesive material 308 would help create a good bond so that the capping device can endure multiple opening and closing without falling down from the injection port.

Figure 11A:
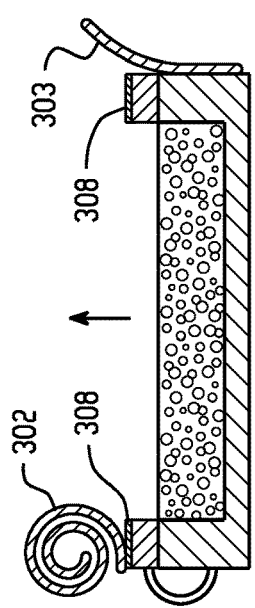
FIG. 11A is a view of the capping device, according to an embodiment, applied to the injection membrane in a closed position.
Figure 11B:
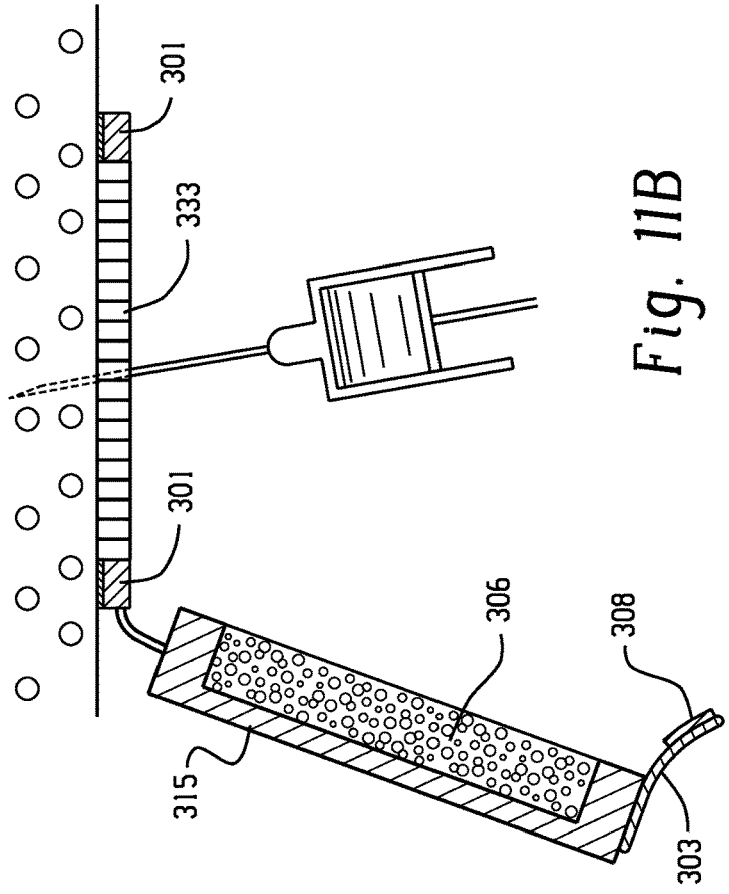
FIG. 11B is a view of the capping device, according to an embodiment, applied to the injection membrane in an open position.

FIG. 11A is cross-sectional view of the capping device 300 closed and applied (taped, glued) around the injection membrane 333. The base 301 is slightly wider than the "belly button" injection membranes known in the art. The height of the base 301 corresponds to the height of the injection membrane 333 so that two of them could create an even surface. The disinfecting pad 306 soaked with the disinfecting agent is showed contacting and sterilizing the injection membrane 333. The bend 305 is short and keeps the cap 315 and the base 301 together. The side extension 303 also keeps the cap 315 and the base 301 together on the opposite side of the bend 305. The side extension 303 attaches to the side of the base 301 and then continues further to attach to the IV bag in proximity to the base 301. It has to be long enough so that the provider can easily grab it and open the cap 315. The tip of the side extension 303 may be intentionally left without the adhesive material to make it easier for the provider to lift it and open the cap 315. At the bottom of FIG. 11 is the capping device 300 shown with the cap 315 open and sterilized (clean) injection membrane, readily available for injection or withdrawal of the medication. The connector (loop, band)) 305 may be made of a durable material to prevent its breakage. The band 305 keeps the cap 315 in proximity to the membrane 333, thus reminding a medical provider to close the cap 315 after each use. As a result, forced compliance with aseptic techniques is achieved, and the rubber injection membrane 333 is always kept sterile.

FIG. 12A shows another version of the capping device 400, according to an embodiment, which serves essentially the same purpose as the embodiment described above. The capping device 400 may include a panel having a front side 402, a back side 403, and a cap 415. The capping device is shown from the side that comes in contact with an injection port 432 and an injection membrane 433 (FIG. 12C). Before the first use, this side may be protected with a peelable foil 401, and in this view, the foil is shown partially peeled.

FIG. 12B shows the capping device with the peelable foil 401 removed, and is ready to be applied to the injection port of the IV bag. The front side 402 of the panel may be covered with an adhesive material, while the back side 403 of the panel is not. The front and back sides 402 and 403 may be connected with the cap 415 through the loop 405. The size and shape of the cap 415 is selected to cover the disinfecting pad 406 and prevent the leakage and evaporation of the disinfecting agent present in the pad. The size and shape of the disinfecting pad 406 correspond to the size and shape of most known injection membranes. The cap 415 may have a side extension 407 disposed on its side opposite to the loop 405. The top surface of the side extension 407 contains an adhesive material, and the adhesive material should allow multiple taping and untaping (gluing and ungluing, affixing and removing) to move the disinfecting pad 406 away, when the injection membrane 433 is in use.

FIG. 12C shows the front side 402 of the panel covered with an adhesive material which is ready to be wrapped around the injection port 432 and the injection membrane 433. The back side 403 of the panel, which does not contain any adhesive material, is also partially seen. The disinfecting pad 405 soaked with the disinfecting agent is illustrated in contact with the injection membrane's inferior surface (where the injection of the medication occurs). This arrangement keeps the membrane sterilized, when the device is not in use. It is very important that the disinfected pad 405 contacts the inferior surface of the injection membrane 433 before the panel (top portion of the invention) is affixed to the injection port 432. In the absence of the contact, there would be an empty space between the membrane 433 and the disinfecting pad 405. The height and length of the panel may vary. The panel may be long enough to wrap around the injection port only once or multiple times for more secure connection. The left or right side of the panel might be of different length viewed from the loop 405. In this case, a shorter side would be affixed to the injection port first and the longer side may be wrapped around it few times.

FIG. 12D is the front view of the disinfecting apparatus 400 affixed to the injection port 432 and the injection membrane 433. The back side of the panel 403 completely covers injection port, but since the capping device is made of very light material that easily bends, it takes the shape of the injection port, especially after the panel is wrapped around the port and light pressure is applied over the panel to secure the connection with the port. The cap 415 is shown closed and the inferior surface of the injection membrane 433 is now in contact with disinfecting pad to sterilize the injection membrane 433. A side extension 407 of the cap is affixed to the back side of the panel 403, which is wrapped around the IV bag injection port. The side extension 407 and the loop 405 in the back keep the cap 415 near the inferior surface of the injection membrane, where the needle penetrates the membrane for injection or withdrawal of the medication.

FIG. 12E shows cross-sectional view of the invention in a closed position. The back side 403 of the panel is shown wrapped around the injection port 432 and injection membrane 433. The loop 405 opposite to the side extension 407 is permanently affixed to the panel. Its length is fairly short and very durable, so that the cap 415 stays near the injection membrane, while allowing for multiple opening and closing of the cap 415 so that the injection membrane 433 can be used when needed. The side extension 407 is shown with the adhesive material disposed on its upper surface, coming into contact with the back side 403 of the panel wrapped around the injection port. The cap 415 is shown as a cross-sectional view with its disinfecting pad contacting the inferior surface of the injection membrane 433 and sterilizing it. When the injection membrane 433 needs to be used for injection or withdrawal, a provider may disconnect the side extension 407 from the injection port, and the cap would be detached so the injection membrane becomes accessible. The loop 405 would keep the cap 415 near the injection membrane, thus reminding the provider to close the cap 415 after use to ensure compliance with sterile techniques. Indeed, the likelihood that a provider would not notice that the cap 415 is hanging and would not close it (tape it to the injection port) is extremely low.

The present inventive concept is not limited to the injection membranes found on intravenous bags (IV bags), and can also be used to disinfect the membranes found on many intravenous tubings, arterial tubings, catheters, and any other piece of medical equipment, where a sharp object penetrates the membrane, and where sterility of the membrane is of utmost importance to prevent bloodstream infection.

In another embodiment, a method for disinfecting a medical injection port is provided. According to the method, a device for disinfection of a medical injection port is provided. The device includes a capping portion having an inner surface, a hollow portion having an inner surface, a proximal opening, and a distal opening, a connector coupling the capping portion of the device to the hollow portion thereof, and a disinfecting absorbent material disposed inside the capping portion of the device. The connector permits movement of the capping portion between a fully-seated position on the hollow portion of the device, and a position apart from the proximal opening thereof to permit ingress to the medical injection port. The method further includes attaching the device to the medical injection port to bring the disinfecting absorbent material in contact with the medical injection port.

The method may further include applying an external force to the device to move the top portion thereof from the fully-seated position to the position apart from the proximal opening of the hollow portion, inserting a medical implement through the proximal opening of the hollow portion of the device into the medical injection port, and withdrawing at least a portion of a content of the medical injection port into the medical implement.

The method may yet further include moving the capping portion of the device from the position apart from the proximal opening to the fully-seated position to bring the disinfecting absorbent material in contact with the medical injection port.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A device for disinfection of a medical injection port having an external end and an injection membrane located at the external end, the device comprising:
    a capping portion comprising
        an opening having a continuous periphery,
        an external surface and a continuous coextensive inner surface facing the external end of the medical injection port, wherein the external surface and the continuous coextensive inner surface are configured to form a cavity extending inwards from the opening, and
        a disinfecting absorbent material disposed inside the capping portion and directly contacting the continuous coextensive inner surface thereof, wherein the disinfecting absorbent material occupies the entire cavity of the capping portion;
    a hollow portion disposed around and in contact with the injection membrane, wherein the injection membrane is located at an end of the medical injection port, and wherein the hollow portion comprises a non-threaded inner surface, a proximal opening having a continuous periphery this is superposable with the continuous periphery of the opening of the capping portion, and a distal opening; and
    a connector coupling the capping portion of the device to the hollow portion thereof in a manner which permits angular movement of the capping portion between
        a fully-seated position on the hollow portion of the device, wherein the continuous periphery of the opening of the capping portion is superposed on the continuous periphery of the proximal opening of the hollow portion such that the injection membrane is encapsulated between the capping portion of the device and the hollow portion thereof to provide a sealed connection therebetween, wherein the disinfecting absorbent material is in a direct and prolonged contact with the injection membrane, and wherein the disinfecting absorbent material completely covers the proximal opening of the hollow portion, and
        a position apart from the proximal opening thereof to permit ingress to the medical injection port.

2. The device of claim 1, wherein the device is configured for attachment to the medical injection port to bring the disinfecting absorbent material of the capping portion in contact with the medical injection port.

3. The device of claim 1, wherein the proximal opening is substantially circular.

4. The device of claim 1, wherein the proximal opening is disposed concentrically to the inner surface of the hollow portion.

5. The device of claim 1, wherein the disinfecting absorbent material is affixed to the inner surface of the capping portion of the device.

6. The device of claim 1, wherein the disinfecting absorbent material is soaked with a disinfecting agent.

7. The device of claim 1, wherein the connector comprises a hinge providing a pivotal connection between the capping portion of the device and the hollow portion thereof.

8. The device of claim 1, wherein a side extension of the capping portion of the device is affixed to the hollow portion thereof in the fully-seated position.

9. The device of claim 1, wherein the connector is adapted such that, when the capping portion is disposed at the position apart from the proximal opening of the hollow portion of the device in the absence of an external force, the connector brings the capping portion to the fully-seated position.

10. The device of claim 1, wherein the connector comprises a flexible material.

* * * * *